US011534569B2

(12) United States Patent
Longest, Jr. et al.

(10) Patent No.: US 11,534,569 B2
(45) Date of Patent: Dec. 27, 2022

(54) COMBINATION DEVICES, SYSTEMS, AND METHODS FOR HUMIDIFICATION OF THE AIRWAYS AND HIGH EFFICIENCY DELIVERY OF PHARMACEUTICAL AEROSOLS

(71) Applicant: VIRGINIA COMMONWEALTH UNIVERSITY, Richmond, VA (US)

(72) Inventors: Philip Worth Longest, Jr., Midlothian, VA (US); Michael Hindle, North Chesterfield, VA (US); Benjamin Spence, Richmond, VA (US); Sneha Dhapare, Henrico, VA (US); Wei Xiangyin, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 462 days.

(21) Appl. No.: 16/617,541

(22) PCT Filed: May 31, 2018

(86) PCT No.: PCT/US2018/035456
§ 371 (c)(1),
(2) Date: Nov. 27, 2019

(87) PCT Pub. No.: WO2018/222912
PCT Pub. Date: Dec. 6, 2018

(65) Prior Publication Data
US 2020/0139074 A1    May 7, 2020

Related U.S. Application Data

(60) Provisional application No. 62/659,985, filed on Apr. 19, 2018, provisional application No. 62/512,750, filed on May 31, 2017.

(51) Int. Cl.
*A61M 16/14* (2006.01)
*A61M 16/10* (2006.01)
(Continued)

(52) U.S. Cl.
CPC .......... *A61M 16/14* (2013.01); *A61M 11/041* (2013.01); *A61M 15/0086* (2013.01);
(Continued)

(58) Field of Classification Search
CPC .............. A61M 16/00; A61M 16/0057; A61M 16/022; A61M 16/0666; A61M 16/08;
(Continued)

(56) References Cited

U.S. PATENT DOCUMENTS 5,277,175 A    1/1994 Riggs et al.
2005/0229928 A1*  10/2005 Ivri ...................... A61M 11/005
                                                                128/203.12

(Continued)

*Primary Examiner* — Joseph D. Boecker
(74) *Attorney, Agent, or Firm* — WCF IP

(57) ABSTRACT

Devices, systems, and methods are disclosed which permit ventilation therapy concurrent with humidity and aerosol drug delivery. Exemplary mixer-heaters employ alternating actuation of humidity and drug nebulizers and may use a single constant power setting for the heating section while keeping a controlled outlet temperature over the course of treatment.

20 Claims, 11 Drawing Sheets

(51) Int. Cl.
*A61M 11/04* (2006.01)
*A61M 16/06* (2006.01)
*A61M 16/16* (2006.01)
*A61M 16/08* (2006.01)
*A61M 16/00* (2006.01)
*A61M 11/00* (2006.01)
*A61M 15/00* (2006.01)

(52) U.S. Cl.
CPC .... *A61M 16/0666* (2013.01); *A61M 16/0816* (2013.01); *A61M 16/1085* (2014.02); *A61M 16/16* (2013.01); *A61M 11/00* (2013.01); *A61M 16/024* (2017.08); *A61M 2016/0018* (2013.01); *A61M 2205/0238* (2013.01); *A61M 2205/3368* (2013.01); *A61M 2206/11* (2013.01)

(58) Field of Classification Search
CPC .......... A61M 16/0816; A61M 16/1085; A61M 16/14; A61M 16/147; A61M 16/16; A61M 11/00; A61M 2016/0018; A61M 2205/3368; A61M 15/0086
See application file for complete search history.

(56) References Cited

U.S. PATENT DOCUMENTS

| | | | |
|---|---|---|---|
| 2010/0074881 A1* | 3/2010 | Boucher | A61P 11/00 514/6.9 |
| 2010/0282247 A1 | 11/2010 | Kadrichu et al. | |
| 2012/0251594 A1* | 10/2012 | Longest | A61P 23/00 424/45 |
| 2015/0007817 A1* | 1/2015 | Longest | A61M 16/1095 128/203.14 |
| 2017/0000965 A1 | 1/2017 | Cortez, Jr. et al. | |
| 2017/0021125 A1 | 1/2017 | MacLoughlin et al. | |
| 2017/0165448 A1* | 6/2017 | Nibhanipudi | A61M 16/16 |

* cited by examiner $t_{exit}$ = 0.23 s $t_{exit}$ = 0.27 s $t_{exit}$ = 0.18 s

COMBINATION DEVICES, SYSTEMS, AND METHODS FOR HUMIDIFICATION OF THE AIRWAYS AND HIGH EFFICIENCY DELIVERY OF PHARMACEUTICAL AEROSOLS

CROSS-REFERENCE TO RELATED APPLICATIONS

This application claims the benefit of U.S. Provisional Patent Application Nos. 62/512,750, filed May 31, 2017, and 62/659,985, filed Apr. 19, 2018. The complete contents of both provisional patent applications are herein incorporated by reference.

STATEMENT REGARDING FEDERALLY SPONSORED RESEARCH OR DEVELOPMENT

This invention was made with government support under Grant No. 2R01HL107333-05A1 awarded by the National Institutes of Health. The government has certain rights in the invention.

FIELD OF THE INVENTION

The invention generally relates to devices and systems which both humidify a subject's airways and provide high efficiency delivery of pharmaceutical aerosols.

BACKGROUND

U.S. Pre-Grant Publication No. 2015-0007817 A1 discloses a prior mixer-heater. A challenge with some embodiments of this prior mixer-heater was the relatively large mixer volume required to accommodate the aerosol before the heating section. The large volume had the advantage of minimizing aerosol loss and was needed for continuous aerosolization. However, the large volume of the previous design could make synchronization of aerosol delivery with inhalation challenging. This is because of a travel time delay between the point of nebulization and the lungs. Only aerosol generated very early in the inhalation cycle could reach the lungs with a mixing volume of ~500-1000 ml, since this is similar to an adult inhaled volume (~500 ml) during passive breathing. High efficiency lung aerosol delivery required deep inhalations.

Difficulties arising from large device and system volumes are not the only issues in existing aerosol systems. While existing HFNC systems effectively deliver humidified air, they are very inefficient at delivering pharmaceutical aerosols. For example, Perry et al. reported ex-cannula aerosol dose was <0.4% of the nominal dose at typical adult HFNC flow rates of 20 LPM and above (Perry S A, Kesser K C, Geller D E, Selhorst D M, Rendle J K and Hertzog J H. Influences of Cannula Size and Flow Rate on Aerosol Drug Delivery Through the Vapotherm Humidified High-Flow Nasal Cannula System. Pediatr. Crit. Care Med. 2013; 14:E250-E256).

Positioning a mesh nebulizer upstream of the HFNC humidity unit, Reminiac et al. achieved 2 to 10% of nebulized dose downstream of an in vitro nasal model (Reminiac F, Vecellio L, Heuze-Vourc'h N, Petitcollin A, Respaud R, Cabrera M, Le Pennec D, Diot P and Ehrmann S. Aerosol therapy in adults receiving high flow nasal cannula oxygen therapy. Journal of Aerosol Medicine and Pulmonary Drug Delivery 2016; doi:10.1089/jamp.2015.1219).

A recent in vivo study of aerosol delivered simultaneously with a commercial HFNC system reported lung delivery efficiencies in the range of 1-4% of the nebulized dose (Dugernier J, Hesse M, Jumetz T, Bialais E, Roeseler J, Depoortere V, Michotte J-B, Wittebole X, Ehrmann S and Laterre P-F. Aerosol delivery with two nebulizers through high-flow nasal cannula: A randomized cross-over single-photon emission computed tomography study. Journal of Aerosol Medicine and Pulmonary Drug Delivery 2017; 30:349-358). Over 50% of the nebulized aerosol was lost in the delivery system.

The lung drug delivery efficiencies from nebulizers in infants is unacceptably low (<5% of the nominal dose delivered to the lungs) and therefore there is a need for the development of more efficient delivery systems synchronized to infant breathing, especially for high dose medications such as antibiotics. Patient-related factors combined with aerosol factors have contributed to poor delivery efficiencies. Continuous nebulization throughout the entire respiratory cycle of infants that have very short inspiratory times and small inhalation:exhalation ratios results in 6-9 times more drug lost than deposited in the lung. Furthermore, aerosol particle sizes of 4-6 μm obtained using conventional nebulizers have been associated with high (~70%) nasal deposition.

SUMMARY

It is desired that a combination mixer-heater device be configured to efficiently deliver inhaled medications to the respiratory system (e.g., lungs) while providing a continuous stream of airflow required for high flow nasal cannula (HFNC) ventilation support or other forms of noninvasive ventilation. While existing HFNC systems effectively deliver humidified air, they are very inefficient at delivering pharmaceutical aerosols. By contrast, some exemplary combination mixer-heater flow passages according to embodiments of the invention have approximately 5% or less depositional loss with an emitted aerosol drug dose from the mixer-heater of 80% or higher.

According to an aspect of some exemplary embodiments, a new mixer-heater flow path has a significantly reduced volume for adults (e.g., <150 ml) and for infants (e.g., <40 ml). With this reduced volume, nearly all of the aerosol generated during an inhalation cycle is able to reach the patient without requiring deep inhalation. If aerosolization occurs over the first half of inhalation, then all of the aerosol may be purged from the mixer-heater and reach the patient.

A challenge with reducing a mixer-heater volume (e.g., to 150 ml or below, or 40 ml or below) is that simultaneously maintaining low depositional loss in the unit is difficult. This is because of the momentum of the mesh nebulizer aerosol stream, or any aerosol stream, which pushes the aerosol into any boundary that is sufficiently close. To address this challenge some exemplary embodiments include one or more of the following aspects:

A cross-stream orientation with a bore diameter that is configured to minimize deposition and at the same time minimize mixer volume. Examples below include support for bore size selection of the mixer-heater for adults and children.

A flow unifier consisting or comprising rotated 3D rod arrays upstream of the mesh nebulizer. Examples below show that (1) the unifier works effectively and (2) unified upstream flow reduces depositional loss.

A unique round or elliptical (in cross section) mixing region coupled with a channel heating region.

Examples below present data (CFD simulations) showing that a round mixing region with a horizontal (rotated) heating region is exemplary for spreading the aerosol for effective heat transfer.

Optimal delivery of the drug aerosol requires synchronizing the mesh nebulizer with inhalation. With high flow nasal cannula therapy (HFNC), or some other forms of noninvasive ventilation such as low flow nasal cannula (LFNC) or continuous positive pressure ventilation, air is delivered constantly. According to an aspect of some exemplary embodiments, feedback control is used to keep the plates at a constant temperature, and this may serve as a standard process.

A primary challenge with a system having a single heating region for all flows (e.g., HFNC gas as well as aerosol) is that a significant amount of energy is required to fully evaporate the aerosol whereas a much smaller amount of energy is used to heat the gas stream when the drug nebulizer is off. For adults, the drug nebulizer may only be on for 0.2-2 s. For infants, the drug nebulizer may only be on for ~0.1 s or less.

The challenge of a single heating region for all flows of a multi-flow system is illustrated well by a specific numeric example. Consider a HFNC configuration in which a plate temperature in the heating region provides 20.7 Watts (W) to a flow stream to evaporate the aerosol and heat the gas flow from 24° C. to a comfortable 32° C. under adult conditions (30 LPM airflow with liquid mass flow rate of 0.4 ml/min). However, when the drug nebulizer is off, a plate temperature in the heating region is required to provide only 4.6 W to heat a humidified gas stream (air and water vapor but not liquid droplets) from 24 to 32° C. This massive difference in required input power during the period when the (medicament aerosol) nebulizer is on versus when the nebulizer is off is due to the very large heat of vaporization of water. When the drug nebulizer is off, providing 20.7 W of power to a humidified gas stream of air flowing at 30 L/min will heat the gas stream from 24° C. to an uncomfortable and likely unsafe temperature of 60° C. (140° F.).

At the time of this disclosure's filing, it is not possible to control the plate temperature of a single aerosol heater in a way that it can swing from providing 20.7 W to 4.6 W over a fraction of a second (e.g., 0.2-1 s for an adult, ~0.1 s or less for an infant). One potential solution to this problem is to have separate heaters for the gas stream and aerosol each with separate feedback controllers; however, this solution is overcomplicated, requiring additional space, costs, and maintenance.

According to an aspect of some exemplary embodiments of the invention, a solution to the preceding problem in multiflow systems having a single heating region is to use an alternating nebulizer system in which one nebulizer is used as a humidity source and one nebulizer is used to deliver the medicament aerosol. Both nebulizers deliver approximately the same aqueous liquid flow rate. One of the two nebulizers is actuated at all times in an alternating manner. When the medicament nebulizer is actuated during a period of inhalation, it supplies the drug and necessary humidity and the separate humidity nebulizer is not actuated. During all remaining times, the humidity nebulizer is actuated to humidify the continuously flowing gas stream and the drug nebulizer is off to avoid wasting medication and improve lung delivery efficiency. In this manner, a constant flow of ventilation gas (measured in L/min or LPM) and nebulizer solution (measured in ml/min) moves through the heating section at all times, requiring a constant power input and avoiding temperature swings.

A feedback control may be used to keep the single plate temperature at a constant value (e.g., provides ~21 W of power for an adult system operating with a nebulization rate of 0.4 ml/min and an airflow rate of 30 LPM) regardless of whether the drug nebulizer is on or off at any given moment. When the drug nebulizer is actuated during a brief inhalation period, sufficient energy is available to fully dry the aerosol and a safe temperature (e.g., of ~32° C.) is provided to the patient. Similarly during the remainder of the breathing cycle when the humidity nebulizer is actuated (and the drug nebulizer is off), the flow stream is humidified from the evaporating droplets and a safe inhalation temperature of 32° C. is maintained. Providing drug and humidity from separate nebulizers thus produces a simplified system with one heating channel (or pathway).

According to an aspect of some embodiments, a very low volume mixer heater (VLVMH) is provided for exceptionally low inhalation volume drug delivery applications (e.g., with infants) to address both issues of synchronization and timing of aerosol delivery together with reducing the aerosol size to minimize aerosol losses.

According to an aspect of some embodiments, the mixing section of a mixer-heater may be preceded by or else include a flow unifier. A flow unifier may be configured as a perforated plate near an air inlet to help unify incoming airflow. The exit of the mixing region may extend along the top of the device to provide a reduction in depositional loss. The heating section may have an elliptical or rectangular cross-section and end with a streamlined taper leading to outlet tubing. The heating section may align with the gravity vector or be perpendicular to the gravity vector. Whichever the orientation, it may be determined using the major axis of the ellipse or rectangle. In other words, the major axis of the ellipse may be aligned (i.e., parallel) to the gravity vector, or the major axis of the ellipse may be perpendicular (i.e., orthogonal) to the gravity vector.

According to an aspect of some embodiments, mixer-heater volume may be 150 ml or less, in some cases 100 ml or less, in some cases 40 ml or less. The mixer-heater volume may be measured starting at the cross-sectional plane which meets the center of the last nebulizer along the flow path and ending where the mixer-heater meets outlet tubing.

DETAILED DESCRIPTION

Exemplary embodiments include combination devices, in particular mixer-heaters, and systems which employ such combination devices. As the name implies, a combination device combines a plurality of constituent elements. In the present case, separate nebulizer outputs and therapeutic flows are combined to address problems such as those set out in the Background above.

Figure 1:
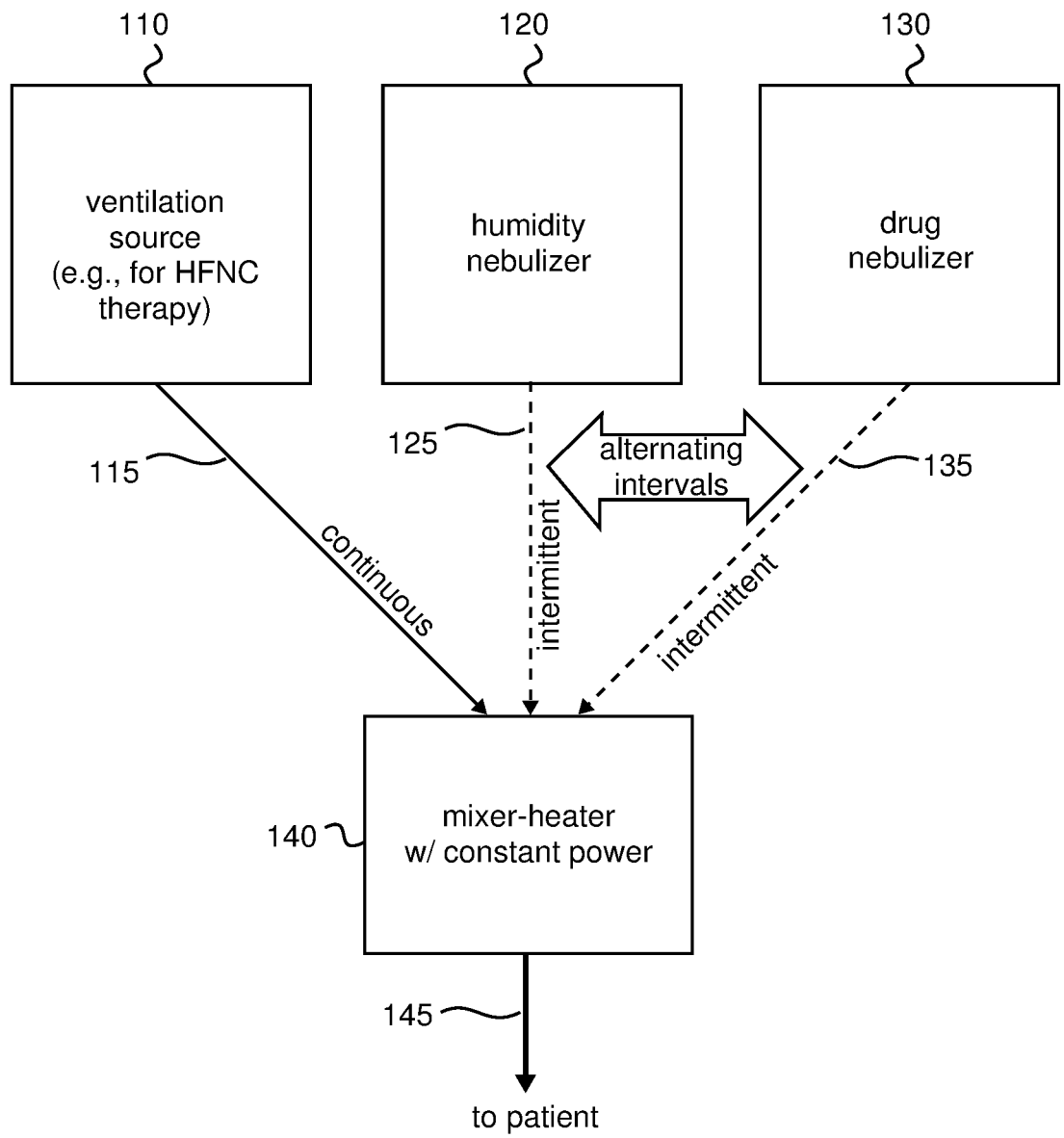
FIG. 1. A block diagram identifying streams and their sources for some exemplary embodiments.

FIG. 1 is a block diagram identifying flows/streams and their sources in some exemplary embodiments directed to combination devices, systems, and methods. At a high level characterization, the mixer-heater 140 serves to combine a minimum of three separately created streams: ventilation stream 115, humidity stream 125, and drug aerosol stream 135. The output of the mixer-heater 140 may be a single output stream 145 which preferably contains uniform humidity, drug dispersion, aerosol droplet or particle size, and temperature. Stream 145 may be referred to as a combined stream or combination stream. In addition, stream 115 may be referred to as the ventilation gas flow, gas flow, or airflow; generally these terms are interchangeable in the context of nasal cannula therapy (e.g., high flow nasal cannula therapy (HFNC) and low flow nasal cannula therapy (LFNC)). The ventilation stream 115 is different and/or separate and apart from the drug aerosol stream 135 and humidity stream 125 before the mixer-heater. Any "stream" may also be referred to interchangeably as a "flow".

The streams 125 and 135 may meet the ventilation gas stream 115 in a cross-flow or cross-stream configuration. The streams 125 and 135 may be introduced approximately perpendicular to the primary direction of streams 115.

A ventilation stream 115 is in and of itself common. A variety of patients requiring medical care today are subject to ventilation systems, especially high flow or low flow nasal cannula therapy (HFNC therapy or LFNC therapy, respectively). A ventilation source 110 supplies a continuous gas stream 115 that is ultimately supplied to the patient through a nasal cannula or other inhalation patient interface (e.g., mask, intubation tube, etc.).

Where exemplary embodiments herein notably deviate from existing HFNC and LFNC ventilation systems is the addition of humidity and drug aerosol streams. Exemplary embodiments combine with a continuous ventilation gas flow 115 both a humidity stream 125 and a drug aerosol stream 135. More specifically, a mixer-heater 140 may operate at a constant heating power setting (e.g., constant wattage) while ventilation stream 115 is continuous, humidity stream 125 is intermittent, and drug aerosol stream 135 is intermittent.

In some preferred embodiments, the intermittent streams 125 and 135 are produced at alternating intervals. While humidity nebulizer 120 is actuated (and thus producing an output), the drug nebulizer 140 is not actuated (and thus not producing an output). Conversely, while drug nebulizer 120 is actuated, the humidity nebulizer 140 is not actuated. The alternating actuation of the nebulizers may also be configured such that the drug nebulizer is actuated in synchrony with part or whole of the patient inhalation cycle while the humidity nebulizer is actuated in synchrony with the remaining time of the breathing cycle or the patient exhalation. The following are acceptable ranges of liquid flow rates from each nebulizer: for a typical adult, 0.8 ml/min to 0.1 ml/min; for children: 0.4 ml/min to 0.01 ml/min; for high dose medications or assuring 100% RH: ~1.2 ml/min to 3 ml/min.

When the drug nebulizer is actuated for the brief periods (e.g., 0.2 s) each inhalation, it provides drug and humidity from the drug formulation, and the humidity nebulizer is off. Drug and humidity nebulizers may deliver the same liquid mass flow rate, e.g., 0.4 ml/min of liquid. In this manner, the same ml/min of liquid (e.g., 0.4 ml/min) is flowing through the heating section at any given time during the course drug delivery to a patient. A constant or substantially constant liquid amount passing the heater enables a constant power input to the heater.

The humidity may be supplied by a first nebulizer 120 and the drug aerosol supplied by a second nebulizer 130. Known nebulizers may be used but frequently produce aerosol droplets which are not sized for efficient administration to the patient, where a target aerosol size is a droplet or particle diameter of approximately 2 µm or below. Straight from the nebulizer, a large percentage of the drug aerosol droplets may deposit on the conduits which conduct the aerosol from the nebulizer to the patient or else deposit at unintended locations of the patient's respiratory tract (e.g., the nose or throat instead of the lung alveoli). An exemplary mixer-heater 140 dries the drug aerosol, thereby reducing droplet size to a predetermined range or below a predetermined threshold. As a result of drying, the size (e.g., mass median aerodynamic diameter, or MMAD) of aerosol droplets is reduced. Reducing the MMAD significantly improves aerosol penetration through the delivery system, patient interface, extrathoracic airways and into the lungs.

Besides drying a drug aerosol, the mixer-heater 140 is importantly configured for supplying a predetermined level of humidity (e.g., expressed as relative humidity, or RH) by combining with the drug aerosol the humidity stream 125 from the nebulizer 120. Predetermined humidity levels may be achieved for conditioning a patient's airways or controlling excipient enhanced growth (EEG) aerosol delivery.

This disclosure distinguishes between continuous streams and intermittent streams. "Continuous" as used herein may mean ongoing without interruption for a predetermined time period (e.g., the full duration, start to finish, of administering nasal cannula therapy to a patient, or of administering/delivering a single dose or round of treatment of a drug to a patient). "Intermittent" may be regarded as the opposite of "continuous" and means one or more intervals exist during the predetermined time period during which the relevant event is not taking place. Generally, "continuous" and "intermittent" are used to describe actuation of a device like a nebulizer or the supply of an airstream or flow. A continuous event may or may not be constant. To illustrate, a continuous air flow over a 10 minute duration may mean that during the 10 minute window the air flow is never zero. However, the airflow may change (e.g., in the first 5 minutes be 20 LPM and in the second 5 minutes be 30 LPM; or cyclically rise and fall in synchronization with a breathing cycle). If a parameter (e.g., flow rate) is constant then the actual numerical value remains the same or substantially the same for the specified duration. An intermittent event may take any of a number of temporal forms, including for example cyclical, sinusoidal, or stochastic. "Alternating" intermittent streams are streams which have a relationship in which, as between two alternating streams, a maximum of one stream is running at any given time. A negligibly small temporal overlap in the alternate intervals may nevertheless occur.

Figure 2:
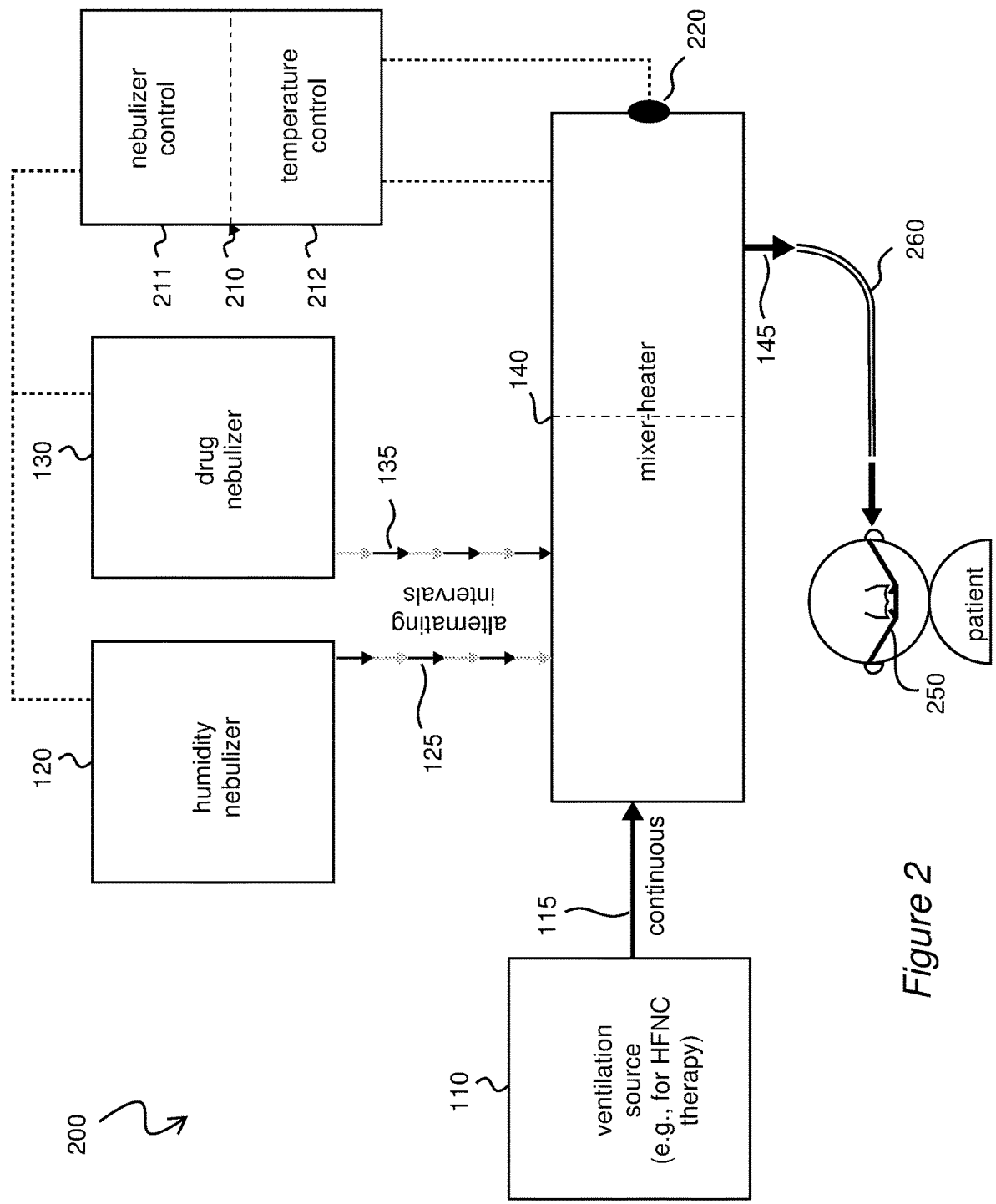
FIG. 2. A block diagram showing an exemplary drug delivery system.

FIG. 2 is a block diagram of an exemplary drug delivery system 200. The system 200 comprises a ventilation source 110, a humidity nebulizer 120, a drug nebulizer 130, and a mixer-heater 140. The nebulizers may be of known types or types developed subsequent to this disclosure. For example, the humidity nebulizer and the drug nebulizer may be mesh nebulizers such as the Aerogen Solo mesh nebulizer.

The system 200 may further comprise a single control unit 210 which may be used to actuate the nebulizers 120 and 130 (e.g., at alternating intervals) and control the power setting (e.g., wattage) of the heating section of the mixer heater 140. Depending on the embodiment, nebulizer control 211 and temperature control 212 may be configured as independent controllers instead of aspects of a unitary control unit 210. The system 200 may comprise one or more temperature probes 220 which may be included and arranged with the mixer-heater 140 so the control unit 210 reliability maintains a constant setting in a feedback loop. The one or more probes 220 may be arranged at the heating element and/or at the outlet of the mixer-heater.

Outlet temperature is central to whether or not a mixer-heater is actually suited for its intended use. In embodiments herein which employ a constant power setting for the heating section, the outlet temperature may be of particular consequence. Too low a temperature may result in incomplete drying of an aerosol and discomfort to a patient. Too high a temperature risks not just discomfort but physical harm to a patient (e.g., burns to airways). Outlet temperature may be measured at the outlet of the mixer-heater 140 and/or the final outlet of the delivery system (e.g., the orifices of the nasal cannula 250 from which the combined stream 145 passes into the patient's airways). In an exemplary embodiment, the mixer-heater is configured to maintain an outlet temperature in the range of 27-42° C., or preferably 28 to 37 (body temp) ° C. In cases involving nasal administration the outlet temperature may be maintained by the mixer-heater in the range of 32±2° C. In actual practice, a mixer-heater may be operated over a startup period that precedes use with a patient. The startup period permits the cannula outlet to reach a temperature corresponding with the mixer-heater temperature and is a function of ventilation tubing length. The mixer-heater outlet and nasal cannula outlet may vary a small amount, e.g., 1 or 2° C. due to cooling in the ventilation conduits; this is within acceptable tolerances for outlet temperature targets after steady state operation is reached.

The flow rate of system 200 may conform to flow rates acceptable for adult high flow nasal cannula (HFNC) therapy. The flow rate of flow 145 which passes through the ventilator tubing 260 to cannula 250 and from there to the adult patient may be, for example, 12-45 LPM, specifically 20 or 30 LPM according to conventional rates at the time this disclosure was written. During a single therapy session, the cannula therapy airflow is generally constant and continuous. In general, flow rate of system 200 may be primarily or entirely determined by the ventilation source 110. Though the humidity nebulizer 120 produces a stream 125 and the drug nebulizer a stream 135, the flow rates of the streams 125 and 135 may be negligible compared to the flow rate of the ventilation stream 115 with which they join in the mixing section of the mixer-heater 140. Specifically, with the use of mesh nebulizers, streams 125 and 135 include no additional net airflow, but inject liquid formulation streams as an aerosol into the mixer, which is denoted in a nebulized liquid flow rate of ml/min.

FIGS. 3A and 3B show two exemplary mixer-heaters, labeled 300 and 350 respectively. Mixer-heater 300 comprises a mixing section 301 and a heating section 302. Similarly, mixer-heater 350 comprises a mixing section 351 and a heating section 352. The mixer-heaters may further comprise inlet sections (303 or 353) and/or outlet sections (304 or 354). In this disclosure the terms "section" and "region" may generally be used interchangeably with respect to subelements of a mixer-heater.

FIGS. 3A and 3B are presented in a drafting style which clearly shows the cross sectional shapes of the flow passages of the mixer-heaters 300 and 350. As may be appreciated from the figures, the shapes of the mixing section and heating section may vary among embodiments. Mixer-heater 300 comprises a mixing section 301 with a circular cross section and a heating section 302 with an elliptical cross-section. By contrast mixer-heater 350 comprises a mixing section 351 the cross-section of which is rectangular with rounded corners (as opposed to sharp corners). Like the heating section 302 of mixer-heater 300, the heating section 352 of mixer-heater 350 is elliptical. Exemplary heating sections may alternatively have a rectangular cross-section, for example, with or without rounded corners.

A primary direction of flow in the mixing section of each mixer-heater is perpendicular to the gravity vector, i.e., flow is substantially horizontal. In fluid communication with the mixing sections are nebulizer inlets 307 and 308. Flows admitted to a mixing section from either nebulizer inlet are introduced by a cross-stream configuration which may facilitate mixing. A mixing region's starting boundary may be treated as the most upstream cross-sectional plane of the mixer-heater at which nebulizer output from inlet 307 (e.g., humidified air) is present. Thus inlet sections 303 and 353 are not part of the mixing section 301 or 351, respectively. Inlet sections 303 and 353 may help with ventilation stream unification prior to the mixing section. In some embodiments the inlet sections 303 and 353 may not be present.

A second mixing section boundary that defines where the section ends may be treated as the most downstream cross-sectional plane of the mixer-heater at which no temperature increase in the combination stream has yet to occur. This same boundary may mark the start of the heater section. Downstream of this boundary the temperature of the combination stream rises. The end boundary of the heater section may be defined as the cross-sectional plane of the mixer-heater at which no further temperature increase occurs. Generally this may correspond with the position along the mixer-heater at which the heating element or elements of the heating section ends. The outlet section at the downstream end of the mixer-heater may be configured to reduce the size of the combination stream to that of the interior of a ventilation tube.

Figure 3A:
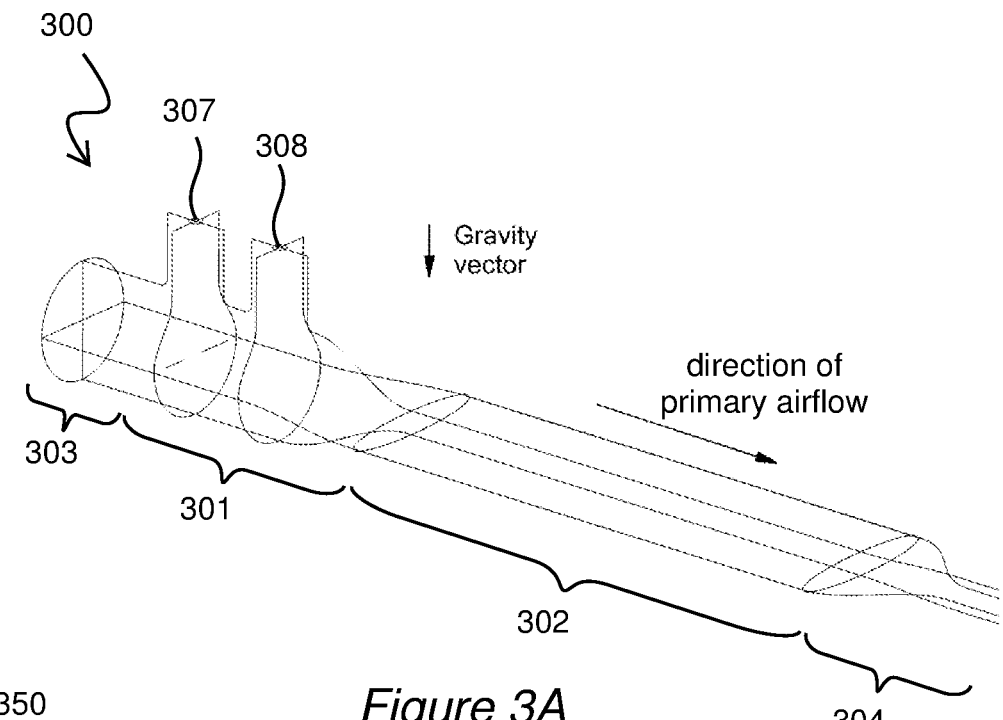
FIG. 3A. A first exemplary mixer-heater.
Figure 3B:
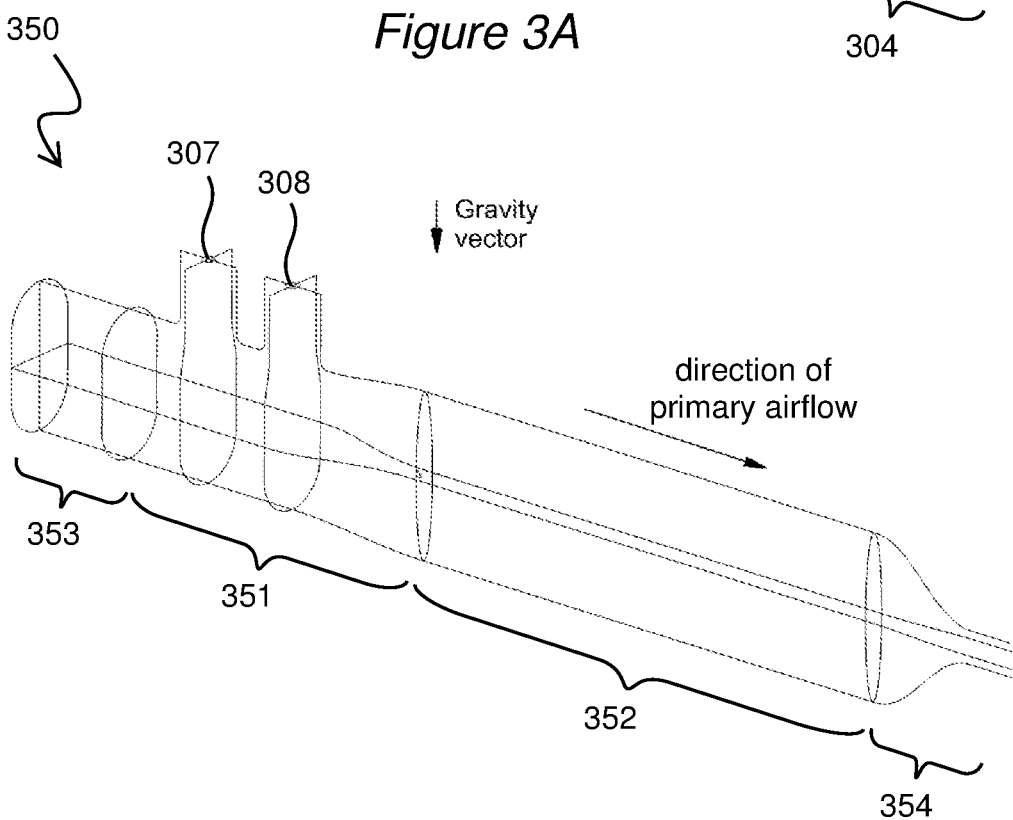
FIG. 3B. A second exemplary mixer-heater.

The direction of flow in the heating section is perpendicular to the gravity vector. However, the long axis of an elliptical heating section's cross section may be either aligned parallel with or perpendicular to the gravity vector. In FIG. 3A, the heating section 302 is perpendicular to the gravity vector. In FIG. 3B, the heating section 352 is aligned parallel with the gravity vector. The lengths of the heating section may vary among embodiments but may be between 10 and 20 mm, for example. Examples below identify a heating section 16 mm in length as exemplary for some applications with adults. The length of a mixing section or heating section may be measured according to the primary direction of airflow.

The geometries of the mixing section and heating section may be aligned. As discussed herein, some exemplary embodiments have an elliptical heating section. Correspondingly, the mixing section may also be elliptical. In such case the major axes of the mixing section and heating section may be aligned in parallel. This arrangement may minimize changes in aerosol direction prior to evaporation in the heating section and thereby minimize depositional losses. In alternative arrangements the major axes of the respective sections may not be aligned in parallel (e.g., major axes may be perpendicular with respect to one another). A horizontal orientation such as is shown in FIG. 3A may improve spreading of the aerosol over the heating channel and thereby improve heat transfer.

The heating section may comprise one or more heating elements, in particular one or more heating plates. In prototype embodiments discussed in the examples below, two plates were employed. The plates may be arranged parallel to one another. The plates may be heated with one or more heaters, for example, Polyimide Film heaters. An insulative material may be provided to shield the plates from the external environment. The insulative material may simply be the shell of the heating section which defines the general geometry and body shape of the flow conducting structure.

The heating section may comprise one or more temperature probes, e.g., thermocouples, to detect the real time temperature of the heating elements. The probes may in turn be connected to a temperature controller. The temperature controller regulates the heater power to attain a set-point temperature of the heating elements. A majority of the supplied energy goes into evaporating the aerosol due to the high heat of vaporization of water (~16 W) with much less energy required to heat a ventilation gas airstream (~5 W). Because either the humidity or drug nebulizer is actuated at all times (but generally there is never a time when both are concurrently actuated), wide temperature swings in the system are avoided as the drug nebulizer cycles on and off, and the system is able attain the thermocouple set-point temperature in a stable manner. The temperature controller may be the same control unit as the nebulizer controller, or the two may be independent control units.

In FIGS. 3A and 3B, mixer-heaters 300 and 350 notably differ in the orientation of the primary axis of their elliptical heating sections. Mixer-heater 300 has a horizontal orientation while the mixer-heater 350 has a vertical orientation. The orientation of the primary axis of the elliptical shaped heating region may involve a tradeoff between evenness of spreading and depositional drug losses. Both effective heat transfer and rapid emptying are desirable attributes of the mixer-heater in addition to minimal depositional drug loss. Therefore, either configuration (horizontal or vertical) may be selected depending on the requirements of a specific application.

A primary characteristic of an exemplary mixer-heater design is a minimized total internal volume, which will improve emptying of the aerosol from a device with limited airflow. Total internal volume of a mixer-heater may be calculated as the sum of its sections, e.g., the combined volumes of mixing section 301, heating section 302, and outlet section 304 for mixer-heater 300 (FIG. 3A). Similarly, the total internal volume of mixer-heater 350 (FIG. 3B) may be determined as the sum of volumes of mixing section 351, heating section 352, and outlet section 354. Improved emptying should minimize the time delay between when the aerosol is generated and when it reaches the patient, thereby improving the lung delivery benefits of synchronization.

For adults, passive inhalation times are typically 1.5 s or greater. An exemplary mixer-heater empties within 20% of this inhalation time, providing an emptying time of 0.3 s or less. To achieve this emptying time at a high-flow nasal cannula (HFNC) flow rate of 20 L/min (LPM) (or 333.3 $cm^3/s$), the total system volume including connective outlet tubing should be 100 ml or less. In reference to FIG. 2, the total volume of the system 200 may include not just the volume of the mixer-heater 140 but also the volumes of any tubing 260 (or other conduits) and cannula 250 (or other patient interface). Any inlet section volume of a mixer-heater may be excluded from the total system volume calculation. At 30 LPM (or 500 $cm^3/s$), an emptying time of 0.3 s can be achieved with a system volume of 150 ml or less. For small children a preferred system volume may be 40 ml or less. While reducing the system volume appears beneficial from an emptying standpoint, it should be realized that the aerosol leaving the mesh nebulizer has observable momentum due to two-way momentum coupling. Therefore, walls of the mixing region should remain sufficiently far from the mesh nebulizer in order to minimize deposition.

Figure 4:
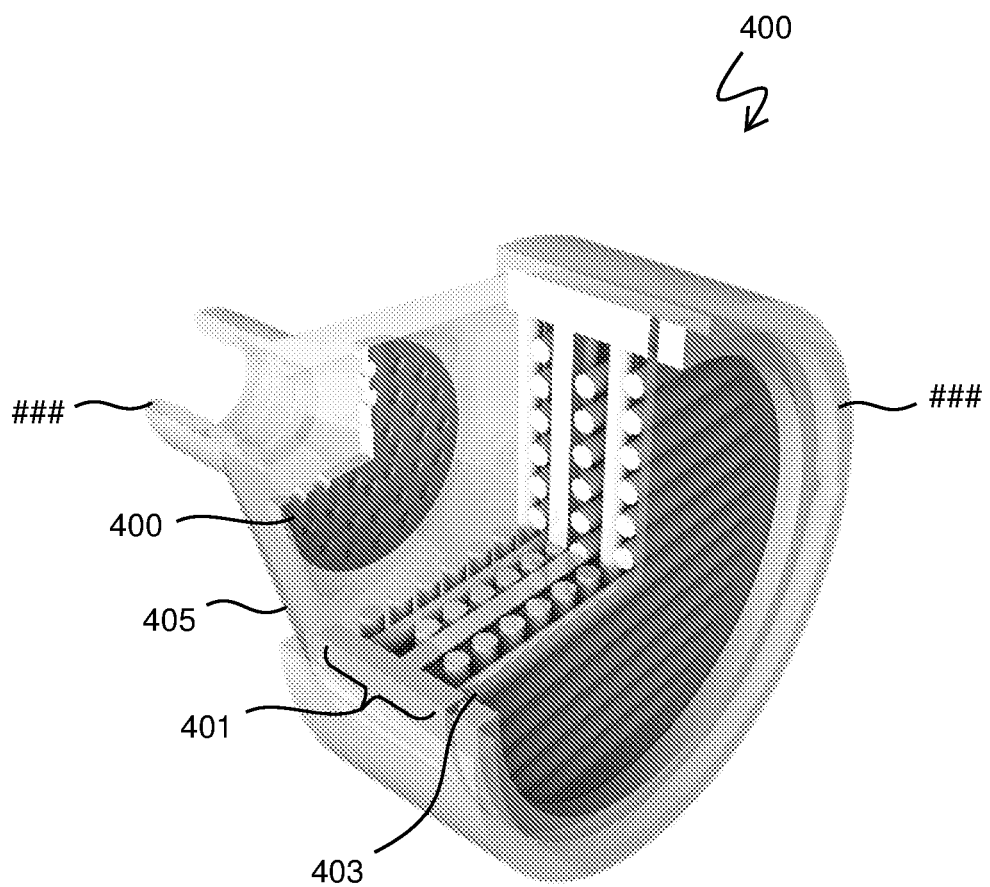
FIG. 4. An exemplary flow unifier.

FIG. 4 shows an exemplary flow unifier 400 which may be arranged upstream of a mixer-heater to unify a ventilation stream that is then admitted to a mixing section of the mixer-heater. Flow unifier 400 may comprise or consists of disks of rod arrays. The rods of a single disk lie in a common plane and are parallel with one another. The rods of adjacent disks lie in separate planes and are rotated 90 degrees with respect to one another, forming a 3D rod array 401. The 3D rod array 401 has three disks of horizontal rods interleaved with three disks of vertical rods. Additional or fewer disks may be used in some embodiments. In additional, the angle of rotation of one disk relative to other disks may be an angle greater than or less than 90 degrees. The flow unifier 400 further comprises an upstream porous plate 403. The plate 403 may not be present in some embodiments. The size (e.g., diameters) of individual rods may be 1-2 mm, for example. The in-plane air gap between rods may be 0.5-1.5 mm, for example. The rod centerlines may be 2.5 to 3 mm apart, for example. The sizes, gaps, and centerline spacing may take other sizes among different embodiments. The flow unifier 400 may comprise additional filter media 403. The flow unifier 400 may further comprise a housing 405 defining the general conduit within which the aforementioned elements are arranged and maintained in fixed positions relative one another. The combination of pressure drop and multiple available flow paths forms a compact, effective, and printable flow unifier.

Figure 5:
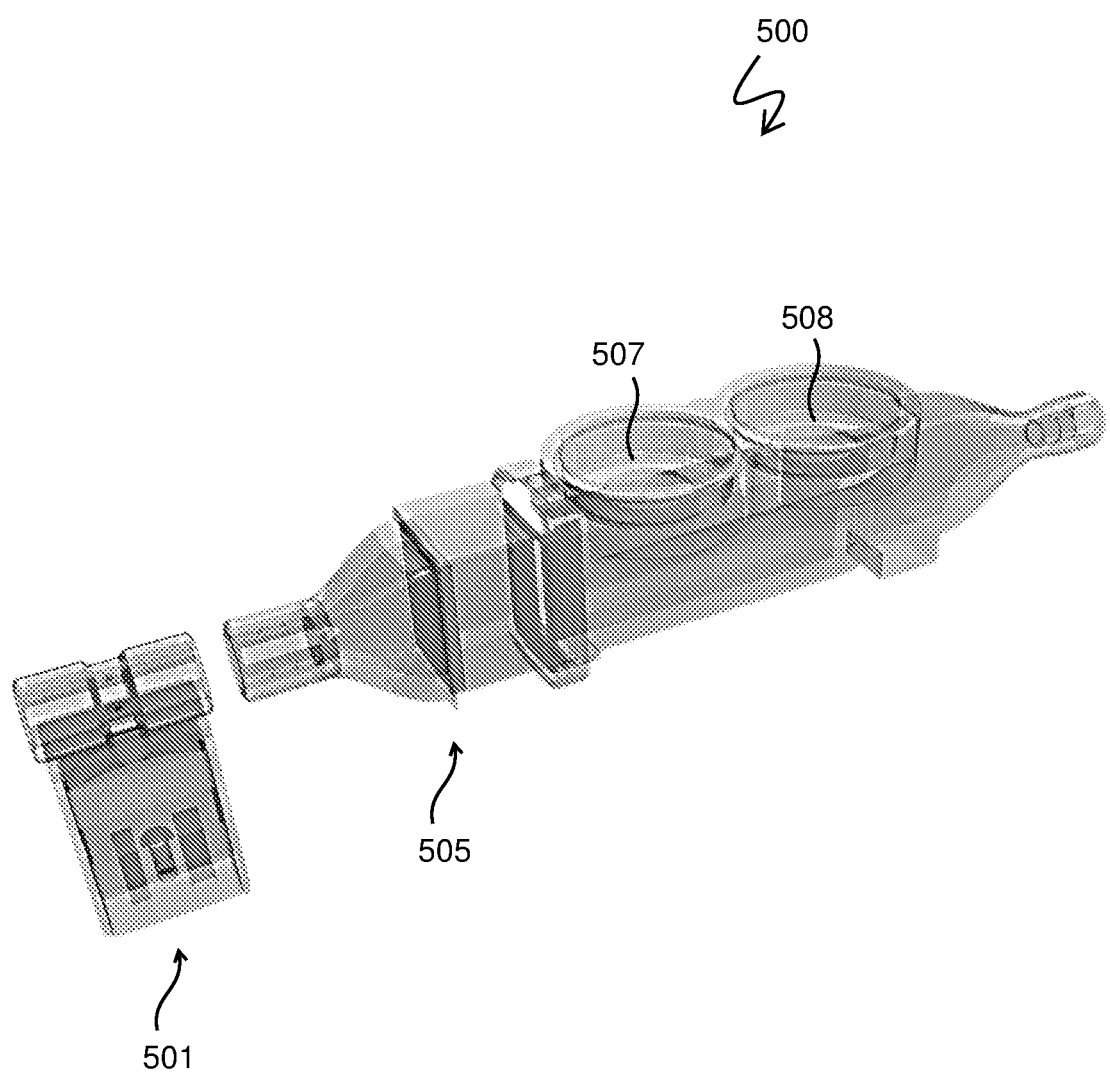
FIG. 5. An exemplary very low volume mixer-heater infant delivery device with a grid inlet for pressurized air at an elevated temperature.

FIG. 5 shows a very low volume mixer heater (VLVMH) 500 usable for exceptionally low volume drug delivery applications (e.g., with infants) to address both issues of synchronization and timing of aerosol delivery together with reducing the aerosol size to minimize aerosol losses. The very low volume mixer heater 500 may have a volume of 10 ml or less, 9 ml or less, 8 ml or less, or 7 ml or less. Example 6 below provides prototype test results for a VLVMH with a volume of 6.7 ml. The prototype embodiment comprised a 10 mm wide and 15 mm tall dryer with a 5 mm air inlet.

In contrast to the exemplary mixer-heaters 300 and 350 discussed above, a VLVMH 500 may have no internal heater. Instead, the VLVMH 500 may be configured for use in a system that includes a heated air source 501 configured to supply heated air of a temperature of 50-90° C. or 50-70° C., for example 60° C. The VLVMH 500 further comprises a grid inlet 505 configured to unify the flow of air into the mixer-heater. The VLVMH 500 is configured to operate with a drug nebulizer connected to inlet 507 and a humidity nebulizer connected to inlet 508 for humidified high-flow therapy by alternating with the drug delivery during treatment.

EXAMPLES

Figure 6A:
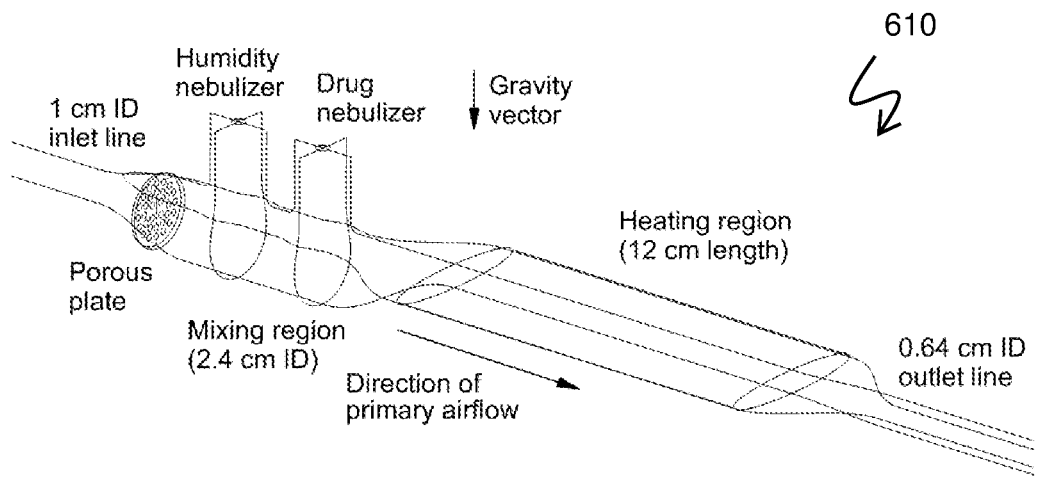
FIG. 6A. A first exemplary prototypical mixer-heater configuration.

Example 1. Flow Path Minimizing Depositional Loss and Maintaining a Volume Below 150 ml Flow Path Geometries A first prototype low-volume mixer-heater 610 is shown in FIG. 6A. The mixer-heater 610 had a 12 cm long heating section. The mixing section included a perforated plate near the 1.0 cm diameter air inlet to help unify the incoming airflow. The exit of the mixing region extends along the top of the device to provide a minor reduction in depositional drug loss for this design. The bore diameter of the initial mixing region was 2.4 cm. As illustrated in FIG. 6A, the heating section has an elliptical cross-section. In the prototype, the heating section had a height of 0.7 cm and length of 12 cm. The heating section ended with a streamlined taper leading to outlet tubing with a diameter of 0.635 cm. The volume of the device starting at the center of the drug nebulizer was 19 ml for the remainder of the mixing section and 40 ml for the heating section including the taper. Including an outlet tubing length of 50 cm, the total mixer-heater volume traversed by the aerosol was 75.0 ml, which is smaller than a 100 ml target volume.

Figure 6B:
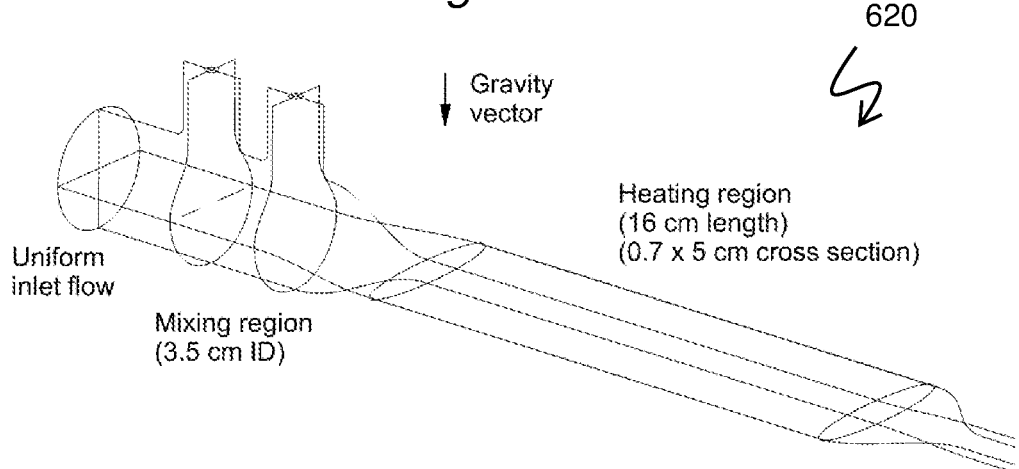
FIG. 6B. A second exemplary prototypical mixer-heater configuration.
Figure 6C:
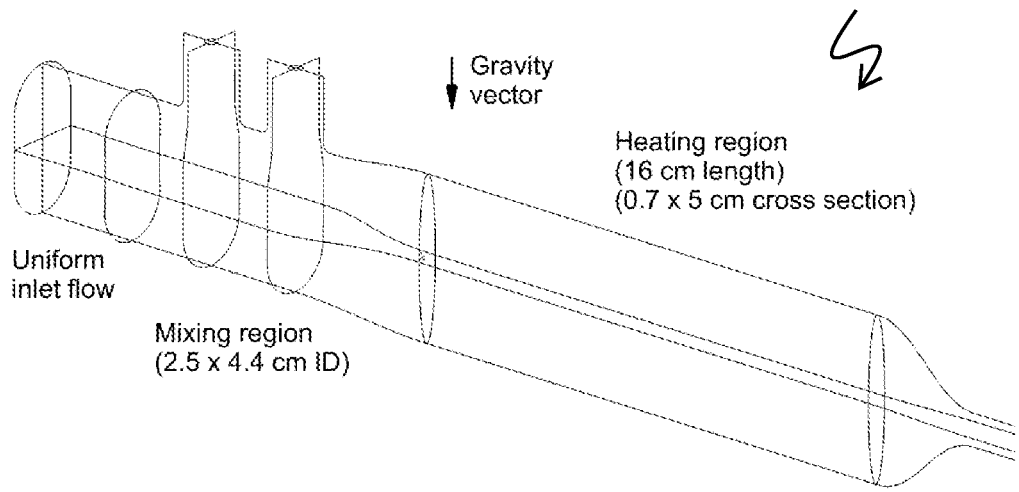
FIG. 6C. A third exemplary prototypical mixer-heater configuration.

Additional mixer-heaters considered include two configurations having 16 cm long heating sections. The first is mixer-heater 620 in FIG. 6B and had a heating section perpendicular to the gravity vector. The second is mixer-heater 630 in FIG. 6C and had a heating section parallel to the gravity vector. Mixer-heater 620 included a uniform inlet velocity profile, larger 3.5 cm internal bore diameter mixing region and longer (16 cm) heating section as compared to the prototype corresponding with FIG. 6A. Mixer-heater 630 included a 2.5×4.4 cm mixing region and a 90 degree rotation of the heating section as compared to mixer-heaters 610 and 620. The vertical orientation of the heating section aligned it with the mixing section. This arrangement may minimize changes in aerosol direction prior to evaporation in the heating section and thereby minimize depositional drug loss. In contrast, the horizontal orientation may improve spreading of the aerosol over the heating channel and thereby improve heat transfer.

Device Control

The prototype mixer-heaters were produced with a heat resistant material using 3D printing. Aerogen Solo mesh nebulizers were used as the separate humidity and drug sources. Actuations of the nebulizers and heating of the airstream was managed with a control unit. Considering nebulizer actuation, a standard Aeroneb Solo driving signal was alternated between the drug and humidity nebulizers at a set timing interval. To capture a wide range of potential adult breathing conditions, the drug nebulizer was actuated for a period of 1.5 s (approximate inhalation phase) followed by a 6 s pause in which the humidity nebulizer was actuated (approximate exhalation phase). As with conventional HFNC therapy, a constant flowrate of 20 or 30 LPM was passed through the system at all times.

The outer shell of the heating section, which was constructed in 3D printed material, contains parallel aluminum heating plates. The parallel aluminum heating plates were heated with Polyimide Film heaters. The two heating plates were in direct contact with the air with the heaters positioned on the back side of the plates next to the 3D printed material, which forms an insulating layer. Use of the metal plates serves to spread the plate temperature evenly, increasing the surface area for effective heat transfer. Approximately 1 cm from the end of the lower plate, a thermocouple was adhered to the metal. The thermocouple was further connected to a temperature controller. The temperature controller regulated the heater power to attain the set-point temperature at the location of the thermocouple.

Experimental Methods

In vitro experiments were used to evaluate all three prototypical low-volume mixer-heaters at flow rates of 20 and 30 LPM. These experiments included determination of depositional drug loss within the device and determination of the outlet drug particle size distribution at the exit of the mixer-heater. Among the nebulizers, the drug nebulizer is positioned nearest the heating section to minimize travel distance (device volume) and therefore maximize delivery of the more valuable medication. In all cases of this example, the drug nebulizer was filled with 0.5% w/v solute consisting 50% w/w albuterol sulfate and 50% w/w sodium chloride. The humidity nebulizer was filled with isotonic saline (0.9% w/v NaCl). The system was typically operated with the humidity nebulizer on for 3 minutes to allow for warm-up and stabilization. After the 3 minute warm-up period, the system was operated in alternating mode with the drug nebulizer actuated for 1.5 s increments followed by 6.0 s increments of the humidity nebulizer.

Both the depositional drug loss within the mixer-heater and aerodynamic particle size distribution of drug aerosols at the outlet were determined using the alternating mode at system flow rates of 20 and 30 LPM. The deposition study was performed by connecting the outlet of the mixer-heater to a low-resistance filter (Pulmoguard II™, Queset Medical, North Easton, Mass.) and a vacuum pump. Particle size distribution was measured by replacing the filter with an Andersen Cascade Impactor (ACI) operated at 28.3 LPM flow condition. In both studies, the drug nebulizer was actuated 60 times to ensure reliable dose collection. The apparatus was dissembled after each run and albuterol sulfate was collected by rinsing the flange of the drug nebulizer, mixer-heater, filter or ACI plates with a known amount of deionized water. The drug nebulizer was weighed before and after the experiment to calculate the nominal delivered dose. Samples were analyzed with HPLC using Allure® PFP Propyl column (5 µm, 2.1×150 mm, Restek Corporation, Bellefonte, Pa.) and 70% methanol: 30% 20 mM ammonium formate buffer with pH adjusted to 3.4 (v/v) as mobile phase (flow rate: 0.4 mL/min). Albuterol sulfate was detected using fluorescence detection at 276 nm excitation (ex) and 609 nm emission (em) (2475 FLR Detector, e2996 PDA detector, e2695 Separation Module, Waters, Milford, Mass.). The injection volume was 100 µL and calibration curves were linear in the range of 0.2-10.0 mcg/mL ($r^2 > 0.999$).

Results

Initial experiments were conducted to determine nebulizer performance. Liquid nebulization rates of three different new Aeroneb Solo nebulizers tested three times each were determined on a gravimetric basis. The nebulizers were filled with 2 ml of a 0.9% w/v NaCl solution and operated for 5 minutes. The mean (standard deviation; SD) liquid nebulization rate was 0.4 (0.02) ml/min. The speed of the aerosol plume exiting the Aeroneb Solo device at a position approximately 2 cm from the mesh (just below the nebulizer outlet flange) was determined using high speed video recordings. The aerosol plume velocity was approximately 3.8 m/s; however, establishing variability was difficult due to inherent transient oscillations. The droplet diameter exiting the Aeroneb Solo device was measured using the ACI operating with near 100% RH air to prevent droplet evaporation. The resulting mean mass median aerodynamic diameter (MMAD) of the initial Aeroneb Solo aerosol with a 0.5% w/v solution of 50% AS and 50% NaCl was 5.3 (0.1) µm with a geometric standard deviation (GSD) of 2.2 (0.4) µm.

Depositional drug loss in each section of the delivery system is reported in Table 1 as a percentage of the nebulized dose of drug. Values are reported as mean (standard deviation) of three or more experiments (n≥3). The outlet filter percentage represents the delivery efficiency out of the mixer-heater device. The mixer-heater 620 reduced depositional loss from ~11% (i.e., the loss from mixer-heater 610) to approximately 5-6%. The mixer-heater 630 further reduced depositional loss to values below 5%. Considering evaporation of the aerosol, all three prototypes effectively reduced aerosol size to approximately 1.5-1.6 µm, which is likely the fully dried size of the polydisperse liquid aerosol once all of the liquid is evaporated and only dried particles of solute remain. The 16 cm prototypes (mixer-heaters 620 and 630) improved device delivery efficiency to approximately 80%, with the best case of >85% achieved by the vertical 16 cm configuration of mixer-heater 630 with 30 LPM airflow.

TABLE 1

Experimentally determined mean (SD) aerosol drug deposition fraction (% of nebulized dose) in different regions of the three mixer-heater designs with a targeted 32° C. outlet temperature and mean (SD) mass median aerodynamic diameter (MMAD) of the aerosol

| configuration | | 20 LPM | 30 LPM |
|---|---|---|---|
| horizontal, 12 cm (610) | Nebulizer (%) | 7.0 (0.7) | 9.1 (0.7) |
| | Mixer-heater (%) | 11.4 (1.2) | 11.1 (0.6) |
| | Outlet filter (%) | 71.1 (2.4) | 71.2 (0.4) |
| | MMAD (µm) | 1.6 (0.0) | 1.5 (0.0) |
| horizontal, 16 cm (620) | Nebulizer (%) | 7.2 (0.7) | 7.0 (1.4) |
| | Mixer-heater (%) | 6.2 (1.6) | 4.5 (1.6) |
| | Outlet filter (%) | 79.2 (4.1) | 80.2 (3.4) |
| | MMAD (µm) | 1.6 (0.0) | 1.5 (0.0) |
| vertical, 16 cm (630) | Nebulizer (%) | 9.3 (1.6) | 9.2 (3.9) |
| | Mixer-heater (%) | 4.4 (1.8) | 4.1 (2.4) |
| | Outlet filter (%) | 80.5 (1.1) | 85.5 (4.7) |
| | MMAD (µm) | 1.6 (0.0) | 1.6 (0.1) |

Example 2. Flow Unifier Performance

Velocity measurements were conducted with a pitot tube pressure measurement device to evaluate the velocity field entering the mixing region. As shown in FIG. 6A, the mixer-heater 610 employed a porous plate to unify the incoming flow. The mixer-heater 620 contained the 3D rod array flow unifier shown in FIG. 4. Successive 2 mm wide disks containing rods with diameters of 1.75 mm were positioned in series with each disk rotated by 90 degrees. On each disk, the rod centerlines are 2.75 mm apart such that the in-plane air gap between rods is 1 mm. Of the 6 disks, the inner two have a rod centerline at the disk center and the outer four have an air gap centerline at the disk center. Ending the unifier is a circular cut of filter media of the same type used in Example 1 (Pulmoguard II™, Queset Medical, North Easton, Mass.). Mixer-heater 630 contained a matching configuration of elements but with a change to the cylindrical or rounded-corner rectangular geometry illustrated in FIG. 6C.

Results

Figure 7:
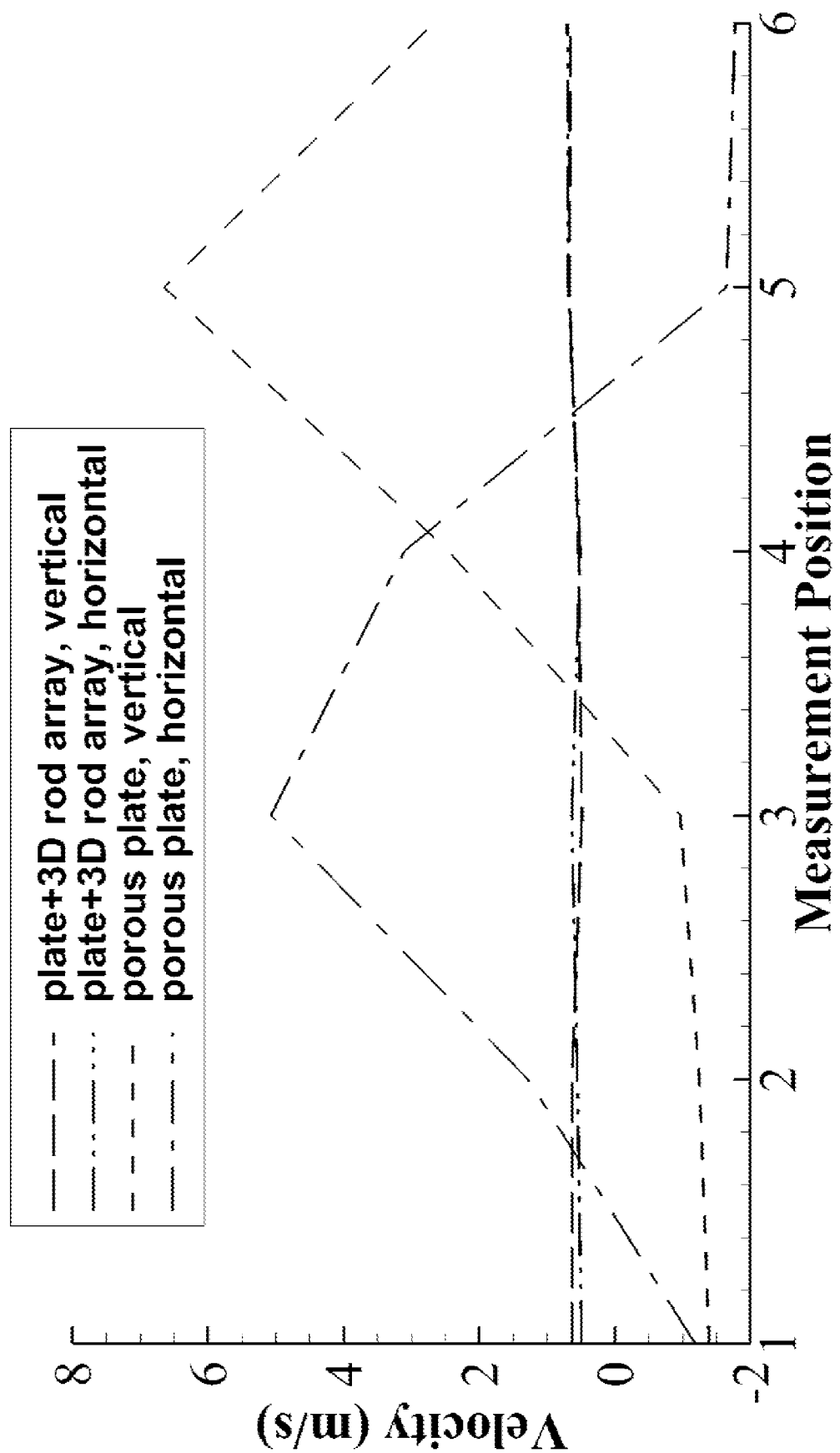
FIG. 7. Pitot tube measurements of velocity in the primary direction of flow on a cross section just downstream of the porous plate (mixer-heater 610 of FIG. 6A) and 3D rod array (mixer-heater 620 of FIG. 6B).

Pitot tube measurements were made at six locations that traversed the mixer-heater inlets downstream of the flow unifier just before the first nebulizer inlet. The measurement locations were determined with a 6-point log-tchebycheff method to accommodate the diameter difference between mixer-heaters 610 and 620. Velocities in the primary direction of flow were measured and converted to standard meter/s velocity units. Velocity values along the flow path vertical and horizontal centerlines are plotted in FIG. 7 for both the mixer-heater 610 (having the porous plate only as unifier)) and the mixer-heater 620 (having the flow unifier 400 of FIG. 4). Vertical and horizontal refer to two linear directions across the cross section. The oval-like unifier for the mixer-heater 630 also performed well in providing an even velocity field across the mixer inlet (note the latter device's data is not plotted in FIG. 7). As indicated in the figure, inclusion of the 3D rod array unit reduces variation in the downstream flow velocity by approximately 1 order of magnitude compared with the porous plate approach.

Example 3. Aerosol Spreading in the Heating Region and Residence Times

Computational fluid dynamics (CFD) simulations were preformed to evaluate transport of droplets through the system. Monodisperse 5.3 µm droplets were injected at the nebulizer inlet with an initial downward velocity of 3.8 m/s, based on experimental measurements. The ventilation gas flow rate through the system was 30 LPM. CFD simulations accounted for turbulent flow, heat and mass transfer, turbulent particle dispersion, and evaporation of the droplets including hygroscopic and solute effects. Grid independence of the hexahedral mesh was established and solution convergence was based on reduction of all residuals by at least three orders of magnitude. All equations were discretized to be at least second order accurate.

Results

Figure 8A:
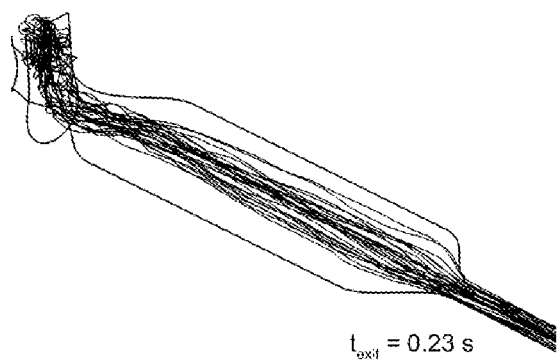
FIG. 8A. Trajectories of injected droplets initialized at the drug nebulizer inlet and carried downstream by a flow rate of 30 L/min while evaporating. Corresponds with the mixer-heater of FIG. 6A.
Figure 8B:
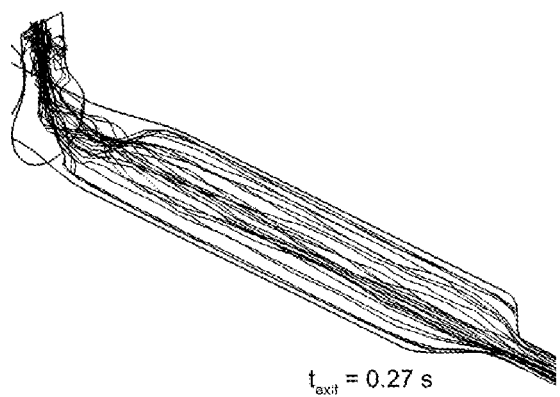
FIG. 8B. Trajectories of injected droplets initialized at the drug nebulizer inlet and carried downstream by a flow rate of 30 L/min while evaporating. Corresponds with the mixer-heater of FIG. 6B.
Figure 8C:
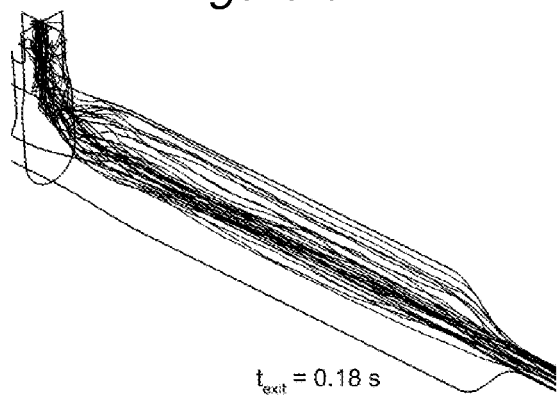
FIG. 8C. Trajectories of injected droplets initialized at the drug nebulizer inlet and carried downstream by a flow rate of 30 L/min while evaporating. Corresponds with the mixer-heater of FIG. 6C.
Figure 9:
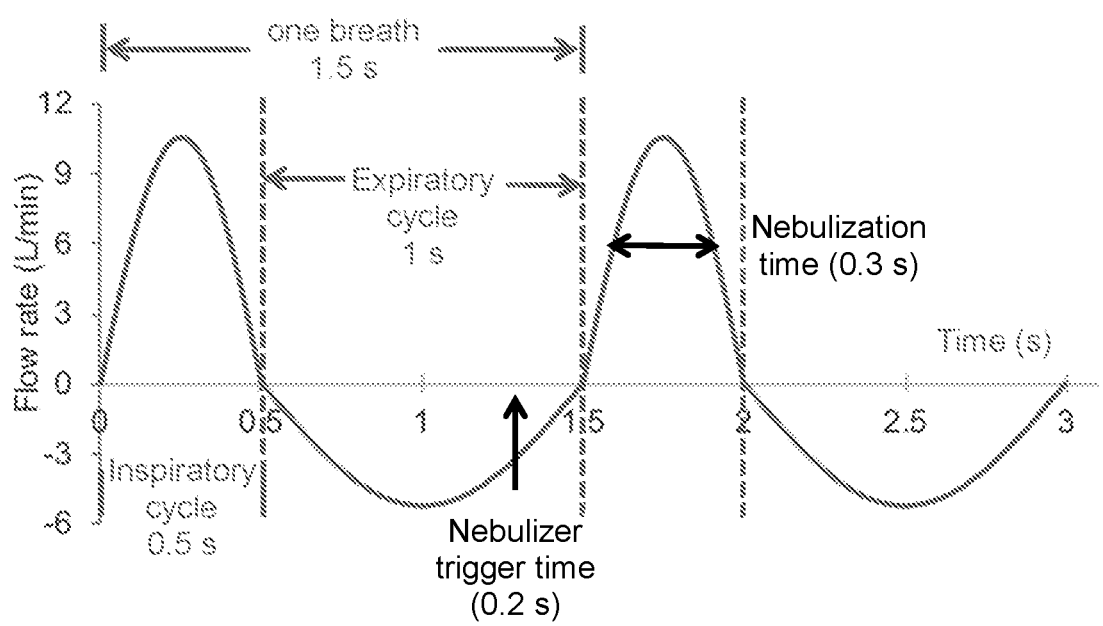
FIG. 9. Flow rate versus time profile of inhalation based on a 8-kg infant showing nebulizer trigger time of 0.2 s and nebulization duration of 0.3 s.

CFD predictions of droplet trajectories illustrate the downward momentum of the nebulized aerosol combined with the cross-flow of ventilation gas. FIGS. 8A to 8C show the trajectories of injected 5.3 μm droplets initialized at the drug nebulizer inlet and carried downstream by a flow rate of 30 L/min while evaporating. FIG. 8A corresponds with mixer-heater 610 of FIG. 6A. FIG. 8B corresponds with mixer-heater 620 of FIG. 6B. FIG. 8C corresponds with mixer-heater 630 of FIG. 6C. In the mixer-heater 610, a tight core of droplets is observed, which represents an inefficient use of the heating channel. The mixer-heater 620 includes a flow unifier and the targeted mixer diameter of 3.5 cm. This reduced and uniform inlet velocity allows the aerosol stream to spread over the entire heating region in the direction normal to primary flow, thereby maximizing heat transfer. The mixer-heater 630 proved less effective at spreading the aerosol stream over the heating region. However, the vertical configuration of the heating channel had the lowest experimentally determined depositional loss (<5%). Thus, the orientation of the primary axis of the elliptical shaped heating region may involve a tradeoff between evenness of spreading and depositional losses.

Average droplet residence time based on CFD predictions is also reported in FIGS. 8A to 8C for the three flow paths considered. The average droplet residence time represents the time required for the droplets to traverse the flow passage from the (drug) nebulizer to the outlet. All designs achieved the target value of <0.3 s. However, of the three prototypes, the vertical design had the lowest residence time value of only 0.18 s.

Example 4. Outlet Temperature Measurements

Current HFNC gas delivery systems are clearly inefficient at delivering inhaled pharmaceutical aerosols. The intent of these systems is to provide gas support at airflow rates of approximately 10 LPM and above in a continuous manner that is warmed and humidified. However, the need for the airstream to be fully saturated with water vapor (100% RH) and at 37° C. for nasal inhalation, as provided by current commercial systems, has not been established. Target performance goals for the mixer heater were output temperatures greater than 32° C. up to 37° C. targeting the nasal valve and anterior turbinate region temperature range of 28–32° C. and % RH>30% to avoid surface irritation due to low osmolarity and liquid sputtering observed with saturated RH. A temperature below 38° C. is preferable for comfort and a temperature below 42° C. is preferable for safety.

Experimental Methods

Temperature and RH were measured at the outlet of the mixer-heater for the alternating operation mode at flow rates of 20 and 30 LPM. Studies were performed with the nominal thermocouple set heating temperatures of 60, 90, 110, 130° C. To capture exiting energy and humidity, a custom shell was prototyped to fit around the temperature and humidity probe tip (M170-HMP75 RH probe, Vaisala, Louisville, Colo.) and the shell positioned the tip parallel with the outlet of the mixer-heater. Temperature and RH measurements were recorded over a 5 minute period after the initial 3 minute startup period and time-averaged values were calculated.

Results

Experimentally measured T and RH values for the mixer-heater 610 with a 60° C. thermocouple temperature are shown in Table 2 for alternating mode delivery (i.e., intermittent delivery). Measured RH values at 20 and 30 LPM were approximately 10% (relative difference) below analytically predicted values, likely because of aerosol depositional loss occurring with the experimental system. However, there was agreement between the measured and CFD predicted values at 30 LPM for both temperature (28.7 vs. 29.0° C.) and RH (40.3 vs. 42.0%). As with the CFD analysis, the desired outlet temperature of 32° C. was not attained in the experiments with a plate thermocouple temperature of 60° C. Further studies were performed at elevated plate temperatures and reveal that the target of >32° C. gas temperatures were achieved for each of the three prototypes (mixer-heaters 610, 620, 630) when operated at plate temperatures between 90-130° C. with flow rates of 20 and 30 LPM. Humidity targets of >30% RH were generally observed, however, the targets was not achieved for the mixer-heater 620 at 30 LPM possibly due to experimental error during humidity reading. In the future, this can be alleviated by small increases in the nebulization rate (liquid flow rate) of the nebulizers above approximately 0.4 ml/min.

TABLE 2

Summary of gas outlet temperatures and relative humidity for mixer-heater prototypes

| | | 20 LPM | 30 LPM |
|---|---|---|---|
| mixer-heater 610 | Set Temperature (° C.) | 60 | 60 |
| | Outlet Temperature (° C.) | 27 (0.1) | 29 (0.2) |
| | Outlet RH (%) | 61 (0.6) | 40 (0.8) |
| mixer-heater 610 | Set Temperature (° C.) | 92 | 93 |
| | Outlet Temperature (° C.) | 33 (0.5) | 32 (0.6) |
| | Outlet RH (%) | 33 (2.1) | 32 (1.7) |
| mixer-heater 620 | Set Temperature (° C.) | 108 | 110 |
| | Outlet Temperature (° C.) | 33 (0.5) | 33 (1.1) |
| | Outlet RH (%) | 39 (1.1) | 21 (3.9) |
| mixer-heater 630 | Set Temperature (° C.) | 128 | 136 |
| | Outlet Temperature (° C.) | 33 (0.3) | 32 (0.5) |
| | Outlet RH (%) | 35 (0.6) | 30 (1.1) |

Example 5. High Efficiency Aerosol Delivery to an Infant with High Respiratory Rate and Low Tidal Volume Using a Very Low Volume Mixer Heater (VLVMH) Experimental Methods Two low volume mixer heater systems were compared for their aerosol delivery performance to an in vitro airway model of a 6-month-old infant via a nasal cannula. A low volume prototype mixer-heater 610 (FIG. 6A) was compared with a prototype mixer-heater 500 (FIG. 5). In both systems, the respective mixer-heater was connected to a streamlined infant nasal cannula via a 22.5 cm length of 0.6 cm internal diameter ventilator tubing. For the mixer-heater 610, it was heated to 60° C. by the lateral heating plates for adequate drying of the aerosol and supplied with pressurized air at 4 LPM. In contrast, the very low volume mixer heater 500 had a smaller volume (6.7 ml) and had the following dimensions: 10 mm wide and 15 mm tall dryer with a 5 mm air inlet. In the VLVMH 500, there were no internal heaters. However, the system was supplied with heated air at a temperature of 60° C. and connected to the streamlined infant nasal cannula via a 22.5 cm length of 0.6 cm internal diameter ventilator tubing. A grid inlet was used to unify the flow of air into the mixer-heaters. Both the mixer-heaters were configured to operate with a second nebulizer for humidified high-flow therapy by alternating with the drug delivery during treatment.

An Aerogen® Solo vibrating mesh nebulizer (Aerogen Limited, Galway, Ireland) was used to generate aerosol into the mixer-heaters in an intermittent delivery mode. The aerosol output of the nebulizer was reduced by altering the voltage input (14.1 Vrms) to produce a rate of approximately 0.07 ml/min to ensure adequate drying of the aerosol, in contrast to the output rate of 0.3 ml/min produced by the original Aerogen® controller. The Aerogen Solo nebulizers were adapted by removing inlet collar walls to minimize the volume between the nebulizer mesh and the inlet of the dryer. The Aerogen® Solo nebulizer was filled with 100 µl of 0.5% w/v albuterol sulfate solution and allowed to run to dryness for each experiment.

The in vitro aerosol delivery experiments were performed using a realistic 6-month-old infant nose-mouth-throat model, which was created from a computed tomography scan of a 7.7 kg male infant and constructed using Mimics® (Materialize, Ann Arbor, Mich.) image segmentation software and CFD. The model anatomy includes nostrils, turbinates, nasopharynx, larynx and a portion of the trachea. Aerosol delivered through the infant nasal model was captured on a low resistance respiratory filter positioned at the exit of the trachea and was considered as the delivered in vitro lung dose. Albuterol sulfate deposition in the mixer heater devices, cannula, infant model and filter was recovered by washing and quantified by HPLC. Losses during exhalation and loss of inhaled dose through exhalation (i.e., drug loss) were estimated based on the difference between the nominal dose and the total recovery of albuterol. Studies were performed in both mixer-heaters to optimize the delivery of aerosolized drug to the simulated in vitro lungs to determine when nebulization should begin in the breathing cycle and the duration of nebulization.

Results

Selection of Nebulization Trigger Point

A breath simulator was used to produce a realistic breathing profile in the airway model. FIG. 6 shows a sinusoidal waveform based on a realistic profile of an 8-kg infant, characterized by 56 mL tidal volume, 0.5 s inhalation, 1 s exhalation and a respiratory frequency of 40 breaths/min and an inspiratory-expiratory ratio of 1:3.18. The time point on the breathing cycle that nebulization was triggered (nebulizer trigger time) was varied in studies with the mixer-heater 610 to synchronize the aerosol delivery from the mixer heater with the breathing cycle, with a goal to determine the trigger point on the respiratory cycle that provides an optimized breath actuated delivery with maximum lung deposition and minimum drug losses. Based on the theoretical delay calculated from the volume of the initial version of the low volume mixer heater device, the volume of the ventilator tubing connecting the mixer-heater to the streamlined cannula and the constant pressurized air flow entrained through the system (4 LPM), actuation times of 0, 0.2, 0.3, 0.4 s prior to inhalation were tested. A relay timer (Macromatic, Menomonee Falls, Wis.), connected to the breath simulator was triggered at the start of the inhalation phase of the breathing cycle to signal the modified controller to actuate the nebulizer. Nebulization duration was 0.1 s. Table 3 shows that triggering the nebulizer for the LVMH simultaneously with the beginning of inhalation (0 s trigger time), resulted in unacceptable drug losses (>90%), with only 1.4% of the aerosol dose delivered to the simulated lung. For this mixer heater, due to the inherent volume of the system, triggering the nebulizer 0.2 s prior to each inhalation was required to maximize delivery to the lungs and minimize losses. While this is experimentally possible using a breath simulator and timing relays, practically, it may not be possible to trigger the nebulizer prior to each patient inhalation. An objective of this delivery system would be to be triggered when the patient begins to inhale. The VLVMH 500 allowed triggering of the nebulizer simultaneously with patient inhalation (0 s trigger time) without the high depositional losses observed in larger volume devices actuated with a 0 s trigger time. Table 3 shows the in vitro lung dose delivered with use of the VLVMH 500 was about 65% of the nominal dose with low losses.

These values were a significant improvement over the current standard of care and larger mixer-heaters. Table 4 compares the aerosol size characteristics of the Aerogen Solo nebulizer and the particle size from the reduced output nebulizers following drying in the mixer-heaters.

TABLE 3

Mean (SD) albuterol sulfate deposition following aerosolization at differing trigger times using the mixer heaters (values a percentage of nominal dose, n = 3-4).

| Device Neb | LVMH (mixer-heater 610) | | | | VLVMH (mixer-heater 500) |
|---|---|---|---|---|---|
| trigger time | 0.4 s | 0.3 s | 0.2 s | 0 s | 0 s |
| Infant model | 5.3 (1.7) | 7.4 (3.4) | 7.2 (2.4) | 4.8 (0.6) | 8.6 (2.5) |
| Lung dose | 16.8 (0.6) | 51.7 (0.8) | 73.9 (4.4) | 1.4 (0.3) | 64.9 (2.2) |
| Drug losses | 77.9 (1.6) | 33.6 (7.5) | 10.4 (2.8) | 93.8 (0.8) | 26.5 (3.3) |

TABLE 4

Mean (SD) aerosol characteristics from the Aerogen ® Solo nebulizer operated at regular output and exiting the tubing of LVMH and VLVMH.

| | Aerogen ® Solo | LVMH | VLVMH |
|---|---|---|---|
| MMAD (µm) | 4.4 (0.1) | 1.1 (0.1) | 0.7 (0.0) |
| GSD (µm) | 1.7 (0.0) | 1.6 (0.1) | 2.1 (0.1) |
| FPF (%) | 60.6 (1.6) | 99.4 (0.2) | 99.1 (0.2) |

Effect of Nebulization Duration on Aerosol Deposition

Figure 10:
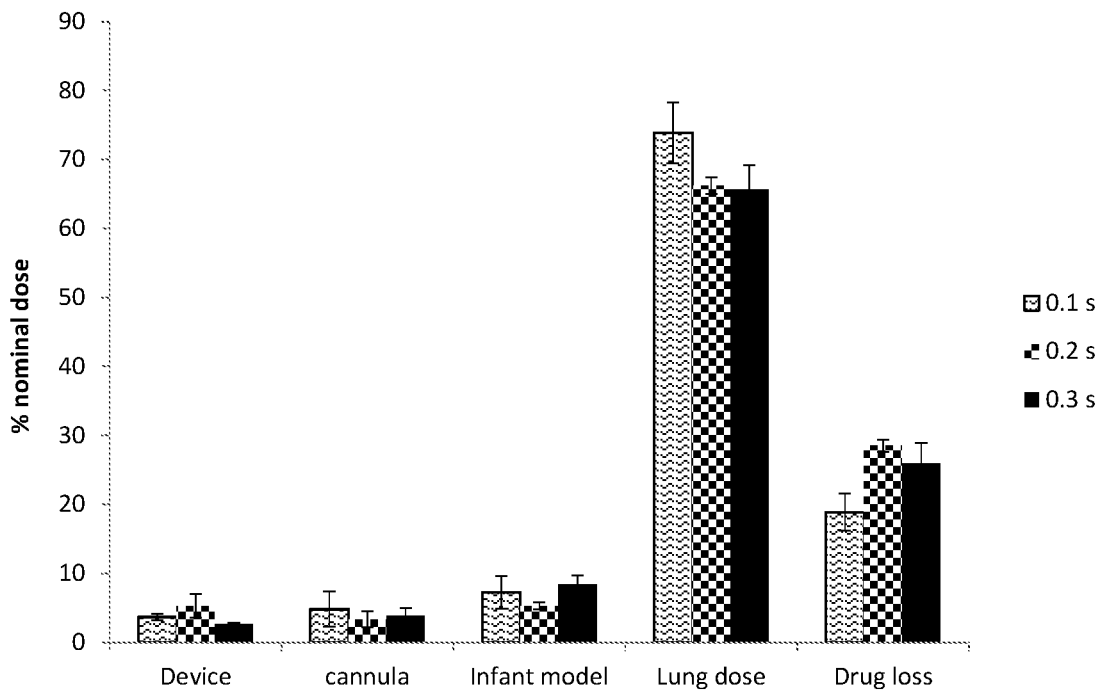
FIG. 10. Albuterol sulfate deposition in delivery device, cannula, infant model, filter (lung dose) and drug loss following aerosolization at different nebulization durations (0.1, 0.2 and 0.3 s) for a low volume mixer heater at nebulizer trigger time of 0.2 s (Data: mean±SD, n=3-5).
Figure 11:
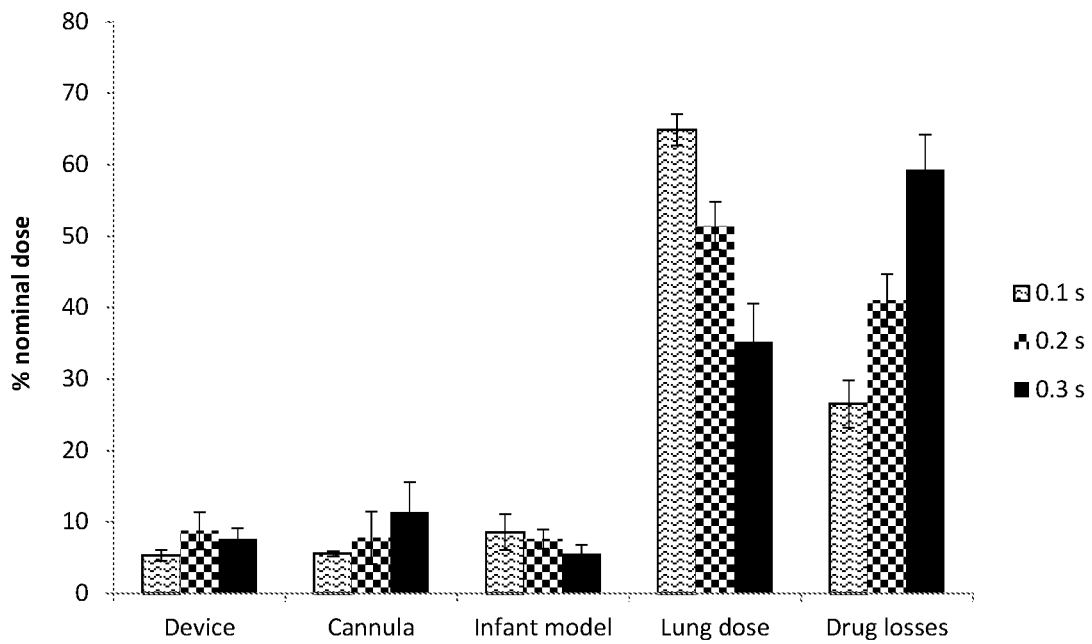
FIG. 11. Albuterol sulfate deposition in delivery device, cannula, infant model, filter (lung dose) and drug loss following aerosolization at different nebulization durations (0.1, 0.2 and 0.3 s) for the very low volume mixer heater shown in FIG. 5 at a nebulizer trigger time of 0 s and a flow rate of 4 L/min (Data: mean±SD, n=3-5).
Figure 12:
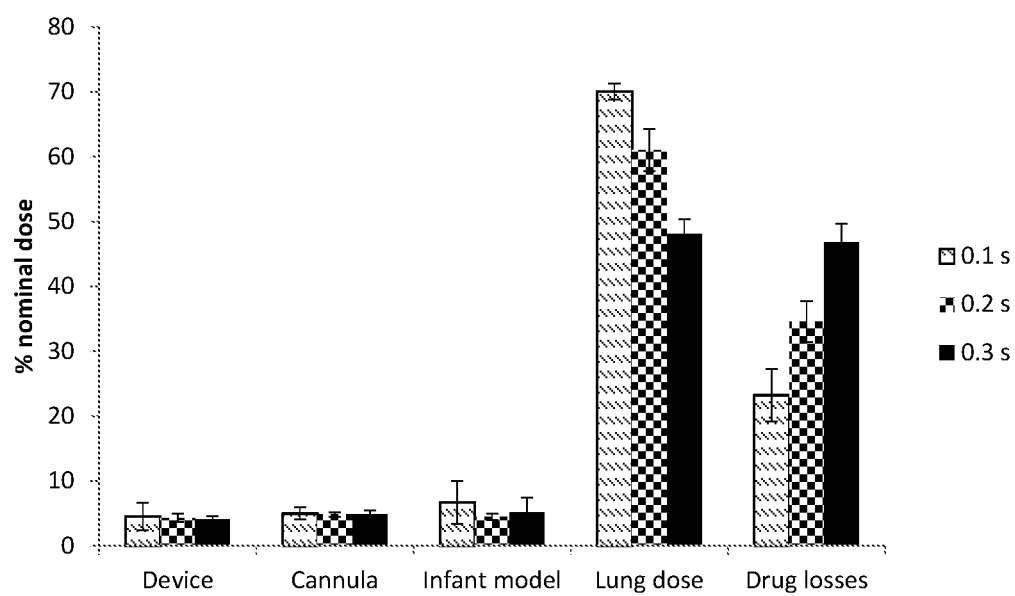
FIG. 12. Albuterol sulfate deposition in delivery device, cannula, infant model, filter (lung dose) and drug loss following aerosolization at different nebulization durations (0.1, 0.2 and 0.3 s) for the very low volume mixer heater shown in FIG. 5 at a flow rate of 6 L/min (Data: mean±SD, n=3-5).

In order to reduce the total aerosol delivery time while achieving maximum lung delivery efficiency, the duration of nebulization was increased in subsequent studies. From the realistic breathing profile, the time during which the inspiratory flow was greater than the entrained airflow of 4-6 LPM, determined to be 0.3 seconds, was hypothesized to enable maximum drug delivery. Accordingly, nebulization durations of 0.1, 0.2 and 0.3 s were investigated to study their effects on aerosol deposition. These were also controlled by a digital relay connected to the breath simulator. Optimized delivery was achieved using the lowest nebulization duration of 0.1 s for each of the mixer heaters as shown in FIGS. 10 and 11. Finally, in order to assess the effect of flow rate through the device on aerosol deposition, flow rate was increased from 4 LPM for VLVMH 500 to 6 LPM. FIG. 12 shows that the in vitro lung deposition increased to ~70% of the nominal dose at 6 LPM compared to ~65% at 4 LPM for the optimized 0.1 s nebulization duration (FIG. 11).

While exemplary embodiments of the present invention have been disclosed herein, one skilled in the art will recognize that various changes and modifications may be made without departing from the scope of the invention as defined by the following claims.

What is claimed is:

1. A drug delivery system, comprising
a first nebulizer configured to intermittently produce a humidity stream;
a second nebulizer configured to intermittently produce a drug aerosol stream;
a mixer-heater comprising
a mixing section configured to combine the humidity stream and the drug aerosol stream with a ventilation stream to produce a combination stream, and
a heating section configured to be operated at a constant power setting without heating the combination stream above 42° C.;
a patient interface configured for delivering the combination stream to a patient; and
one or more conduits fluidically connecting the mixer-heater with the patient interface;
wherein a volume of the mixer-heater, a volume of the one or more conduits, and a volume of the patient interface add up to a system volume of 150 mL or less.

2. The drug delivery system of claim 1, wherein drug delivery system is configured to deliver a constant combination stream to the patient over a single course of patient treatment.

3. The drug delivery system of claim 2, wherein the patient interface is a nasal cannula, and wherein the single course of patient treatment is high flow nasal cannula therapy (HFNC).

4. The drug delivery system of claim 1, further comprising a controller configured to regulate the first nebulizer, second nebulizer, and heating section such that the humidity stream and drug aerosol stream are produced in alternating intervals.

5. The drug delivery system of claim 1, wherein the system volume is 40 ml or less.

6. The drug delivery system of claim 1, further comprising a flow unifier configured to modify the ventilation stream prior to the ventilation stream's admission to the mixing section of the mixer-heater.

7. The drug delivery system of claim 6, wherein the flow unifier comprises a three-dimensional rod array.

8. The drug delivery system of claim 1, wherein the heating section is configured to be operable such that outlet temperature is maintained in a range of 27 to 42° C.

9. The drug delivery system of claim 1, wherein the heating section is configured to be operable such that outlet temperature is maintained in a range of 28 to 37° C.

10. The drug delivery system of claim 1, wherein the heating section is configured to be operable such that outlet temperature is maintained in a range of 32±2° C.

11. A method of drug delivery with ventilation therapy, comprising
intermittently producing a humidity stream with a first nebulizer;
intermittently producing a drug aerosol stream with a second nebulizer, wherein the humidity stream and drug aerosol stream are produced in alternating intervals;
with a mixer-heater,
mixing the humidity stream and the drug aerosol stream with a ventilation stream to produce a combination stream, and
heating the combination stream to a temperature not exceeding 42° C. with a heating section operated at a constant power setting; and
delivering the combination stream to a patient using a patient interface and one or more conduits,
wherein the combining, mixing, heating, and delivering steps use 150 mL or less total system volume.

12. The method of claim 11, wherein the step of delivering comprises delivering a constant combination stream to the patient over a single course of patient treatment.

13. The method of claim 12, wherein the patient interface is a nasal cannula, and wherein the single course of patient treatment is high flow nasal cannula therapy (HFNC).

14. The method of claim 11, further comprising regulating the first nebulizer, second nebulizer, and heating section with a controller.

15. The method of claim 11, wherein the system volume is 40 ml or less.

16. The method of claim 11, further comprising modifying the ventilation stream with a flow unifier prior to the ventilation stream's admission to the mixing section of the mixer-heater.

17. The method of claim 16, wherein the flow unifier comprises a three-dimensional rod array.

18. The method of claim 11, wherein the step of heating heats the combination stream to an outlet temperature in a range of 27 to 42° C.

19. The method of claim 11, wherein the step of heating heats the combination stream to an outlet temperature in a range of 28 to 37° C.

20. The method of claim 11, wherein the step of heating heats the combination stream to an outlet temperature in a range of 32±2° C.

* * * * *